United States Patent
Watanabe et al.

(10) Patent No.: US 6,743,814 B2
(45) Date of Patent: Jun. 1, 2004

(54) NEMATICIDAL TRIFLUOROBUTENES

(75) Inventors: Yukiyoshi Watanabe, Tochigi (JP); Koichi Ishikawa, Tochigi (JP); Shinichi Narabu, Ibaraki (JP); Takuya Gomibuchi, Ibaraki (JP); Yuichi Otsu, Tochigi (JP); Katsuhiko Shibuya, Tochigi (JP)

(73) Assignee: Nihon Bayer Agrochem K.K., Tokyo (JP)

( * ) Notice: Subject to any disclaimer, the term of this patent is extended or adjusted under 35 U.S.C. 154(b) by 0 days.

(21) Appl. No.: 10/220,775

(22) PCT Filed: Mar. 8, 2001

(86) PCT No.: PCT/IB01/00331
§ 371 (c)(1),
(2), (4) Date: Sep. 5, 2002

(87) PCT Pub. No.: WO01/66529
PCT Pub. Date: Sep. 13, 2001

(65) Prior Publication Data
US 2003/0109563 A1 Jun. 12, 2003

(30) Foreign Application Priority Data

Mar. 9, 2000 (JP) ........................................ 2000-064615
Aug. 9, 2000 (JP) ........................................ 2000-240855

(51) Int. Cl.$^7$ .................... A61K 31/421; C07D 263/30; A61P 33/00
(52) U.S. Cl. ........................ 514/376; 548/229; 548/230
(58) Field of Search .............. 548/229, 230; 514/376

(56) References Cited

U.S. PATENT DOCUMENTS

| | | | |
|---|---|---|---|
| 3,513,172 A | 5/1970 | Brokke | ........................ 260/302 |
| 3,697,536 A | 10/1972 | Brokke | ................... 260/302 R |
| 4,952,580 A | 8/1990 | Martinez et al. | |
| 5,273,988 A | 12/1993 | Turnbull | ..................... 514/375 |
| 5,389,680 A | 2/1995 | Ruminski | .................... 514/563 |
| 5,457,134 A | 10/1995 | Ruminski | .................... 514/671 |
| 5,561,162 A | 10/1996 | Ruminski | .................... 514/627 |
| 5,623,084 A | 4/1997 | Ruminski | ...................... 558/54 |
| 5,693,865 A | 12/1997 | Ruminski | .................... 564/484 |
| 5,714,517 A | 2/1998 | Ruminski | .................... 514/563 |

FOREIGN PATENT DOCUMENTS

| | | |
|---|---|---|
| EP | 0 342 150 | 11/1989 |
| EP | 0342150 A1 * | 11/1989 |
| GB | 2 270 688 | 3/1994 |
| GB | 2 270 689 | 3/1994 |
| JP | 10-287659 | 10/1998 |
| WO | 95/24403 | 9/1995 |
| WO | 99/52882 | 10/1999 |
| WO | 01/02378 | 1/2001 |

OTHER PUBLICATIONS

J. Org. Chem. (month unavailable) 1988, 53, pp. 1113–1114 Synthesis and Crystal Structure of 4–tert–Butyl–2 (3H)–oxazolethione, Subramaniam Mohanraj, Warren T. Ford, Paul J. Wooldridge, and Elizabeth M. Holt.

Collection Czechoslovak Chem. Commun. vol. 48 (month unavailable) 1986 pp. 3421–3425 Synthesis and Stability of 2–Oxoisothiocyanates, Vladimir Bobosik, Anna Piklerova and Augustin Martvon.

Canadian Journal of Chemistry vol. 50, (month unavailable) 1972 pp. 3082–3083 Five–membered Heterocyclic Thiones. Part II. Oxazole–2–thione, G. Lacasse and J. M. Muchowski.

Ukrain Khim Zhur, 16, (month unavailable) 1950 pp. 545–551.

J. Med. Chem. (month unavailable) 1994, 37, pp. 322–328 Synthesis and Biological Evaluation of 5–[[3,5–Bis(1,1–dimethylethyl)–4–hydroxyphenyl]methylene]oxazoles, –thiazoles, and –imidazoles: Novel Dual 5–Lipoxygenase and Cyclooxygenase Inhibitors with Antiinflammatory Activity, Paul C. Unangst, David T. Connor, Wiaczelslaw A. Cetenko, Roderick J. Sorenson, Catherine R. Kostian, Jagadish C. Sircar, Clifford D. Wright, Denis J. Schrier, and Richard D. Dyer.

\* cited by examiner

*Primary Examiner*—R Desai
*Assistant Examiner*—Robert Shiao
(74) *Attorney, Agent, or Firm*—Richard E. L. Henderson

(57) ABSTRACT

The present invention relates to novel trifluorobutenes of the formula (I)

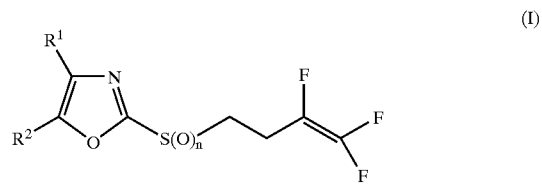

(I)

wherein $R^1$ represents hydrogen; halogen; alkyl that is unsubstituted or substituted with halogen, hydroxy, alkoxy, alkylthio, alkylcarbonyloxy, haloalkylcarbonyloxy, or cyano; alkylsulfonyloxy; or phenyl that is unsubstituted or substituted with halogen, alkyl, haloalkyl, alkoxy, alkylthio, alkylsulfonyl, haloalkoxy, haloalkylthio, phenyl, phenoxy, cyano, or nitro;

$R^2$ represents hydrogen; halogen; alkyl that is unsubstituted or substituted with alkoxy or halogen; or alkoxycarbonyl; and n represents 0, 1 or 2, with the proviso that if $R^1$ represents alkyl, then $R^2$ does not represent halogen. The invention also relates to processes for their preparation and their use as nematicides.

8 Claims, No Drawings

NEMATICIDAL TRIFLUOROBUTENES

The present invention relates to novel trifluorobutenes, processes for their preparation and their use as a nematicidal agent.

Japanese Laid-open Patent Publication No. 85267/1990 describes substituted azolethioethers which have insecticidal activity. U.S. Pat. No. 3,513,172 describes that some kinds of trifluorobutenyl compounds have nematicidal activity and Japanese Laid-open Patent Publication (PCT) No. 500037/1988 describes that some kinds of polyhaloalkene compounds have nematicidal activities. Further, WO 95/24403 describes that 4,4-difluorobutenyl compounds have nematicidal activity.

There have now been found novel trifluorobutenes of formula (I)

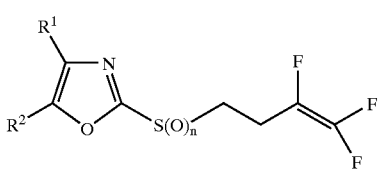

wherein
  $R^1$ represents hydrogen, halogen, or alkyl which may be unsubstituted or substituted with halogen, hydroxy, alkoxy, alkylthio, alkylcarbonyloxy, haloalkylcarbonyloxy or cyano, or represents alkylsulfonyloxy or represents phenyl which may be unsubstituted or substituted with halogen, alkyl, haloalkyl, alkoxy, alkylthio, alkylsulfonyl, haloalkoxy, haloalkylthio, phenyl, phenoxy, cyano or nitro.
  $R^2$ represents hydrogen, halogen, or alkyl which may be unsubstituted or substituted with alkoxy or halogen, or represents alkoxycarbonyl, and
  n represents 0, 1 or 2.
  provided that if $R^1$ represents alkyl, $R^2$ does not represent halogen.

In the definitions, the hydrocarbon chains, such as alkyl, are in each case straight-chain or branched. Substituents may be identical or different.

Preferred substituents or preferred ranges of the radicals present in the formulae listed above and below are defined below.
  $R^1$ preferably represents hydrogen or halogen, or represents $C_{1-6}$ alkyl which may be unsubstituted or substituted with halogen, hydroxy, $C_{1-3}$ alkoxy, $C_{1-3}$ alkylthio, $C_{1-3}$ alkylcarbonyloxy, trifluoromethylcarbonyloxy or cyano, or represents $C_{1-4}$ alkylsulfonyloxy or represents phenyl which may be unsubstituted or substituted with halogen, methyl, trifluoromethyl, methoxy, methylthio, methylsulfonyl, trifluoromethoxy, trifluoromethylthio, phenyl, phenoxy, cyano or nitro.
  $R^2$ preferably represents hydrogen or halogen or represents $C_{1-6}$ alkyl which may be unsubstituted or substituted with $C_{1-3}$ alkoxy or halogen, or represents $C_{1-4}$ alkoxycarbonyl.
  n preferably represents 0 or 2.
  $R^1$ particularly preferably represents hydrogen, fluoro, chloro or bromo, or represents $C_{1-4}$ alkyl which may be unsubstituted or substituted with fluoro, chloro, bromo, hydroxy, $C_{1-3}$ alkoxy, $C_{1-3}$ alkoxy, $C_{1-3}$ alkylthio, $C_{1-3}$ alkylcarbonyloxy, trifluoromethylcarbonyloxy or cyano, or represents methylsulfonyloxy or ethylsulfonyloxy or represents phenyl which may be unsubstituted or substituted with fluoro, chloro, bromo, methyl, trifluoromethyl, methoxy, methylthio, methylsulfonyl, trifluoromethoxy, trifluoromethylthio, phenyl, phenoxy, cyano or nitro.
  $R^2$ particularly preferably represents hydrogen, fluoro, chloro or bromo or represents $C_{1-4}$ alkyl which may be unsubstituted or substituted with $C_{1-3}$ alkoxy or bromo or represents $C_{1-3}$ alkoxycarbonyl.
  n particularly preferably represents 0.

The novel compounds of the above-mentioned formula (I) are obtained, for example, by the following preparation processes a), b), c), d), e), f), g) or h).

Preparation Process a)

Compounds of the formula (I)

wherein $R^1$ represents hydrogen, represents alkyl which may be substituted with halogen, hydroxy, alkoxy, alkylthio, alkylcarbonyloxy, haloalkylcarbonyloxy or cyano or represents phenyl which may be substituted with halogen, alkyl, haloalkyl, alkoxy, alkylthio, alkylsulfonyl, haloalkoxy, haloalkylthio, phenyl, phenoxy, cyano or nitro,
  $R^2$ represents hydrogen or represents alkyl which may be substituted with alkoxy or halogen and
  n represents 0 are obtained when compounds of the formula (II)

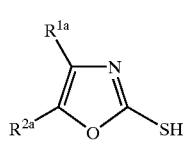

wherein $R^{1a}$ represents hydrogen, represents alkyl which may be substituted with halogen, hydroxy, alkoxy, alkylthio, alkylcarbonyloxy, haloalkylcarbonyloxy or cyano or represents phenyl which may be substituted with halogen, alkyl, haloalkyl, alkoxy, alkylthio, alkylsulfonyl, haloalkoxy, haloalkylthio, phenyl, phenoxy, cyano or nitro,
  $R^{2a}$ represents hydrogen or represents alkyl which may be substituted with alkoxy or halogen and
  n represents 0 are reacted with 4-bromo-1,1,2-trifluoro-1-butene in the presence of inert solvents and if appropriate, in the presence of an acid binder.

Preparation Process b)

Compounds of the formula (I)

wherein $R^1$ and $R^2$ are as defined above, and
  n represents 1 or 2 are obtained when compounds of the formula (Ia)

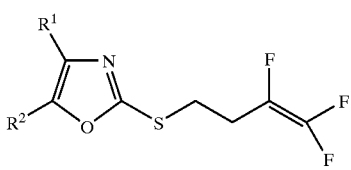

(Ia)

wherein
$R^1$ and $R^2$ are as defined above
are oxidized in the presence of inert solvents.
Preparation Process c)
Compounds of the formula (I)
wherein
$R^1$ represents hydrogen or haloalkyl,
$R^2$ represents halogen, and
n represents 0
are obtained when compounds of the formula (Ib)

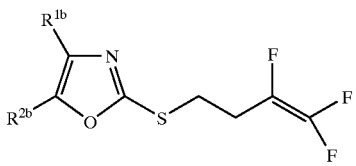

(Ib)

wherein
$R^{1b}$ represents hydrogen or alkyl, and
$R^{2b}$ represents hydrogen
are reacted with a halogenating agent in the presence of inert solvents.
Preparation Process d)
Compounds of the formula (I)
wherein
$R^1$ represents haloalkyl,
$R^2$ represents hydrogen or haloalkyl and
n represents 0
are obtained when compounds of the formula (Ic)

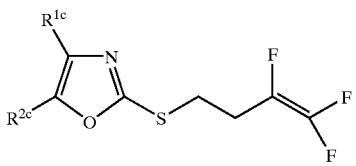

(Ic)

wherein
$R^{1c}$ represents alkyl, and
$R^{2c}$ represents hydrogen or alkyl,
are reacted with a halogenating agent in the presence of inert solvents.
Preparation Process e)
Compounds of the formula (I)
wherein
$R^1$ represents halogen,
$R^2$ represents hydrogen or alkyl and
n represents 0, are obtained when compounds of the formula (III)

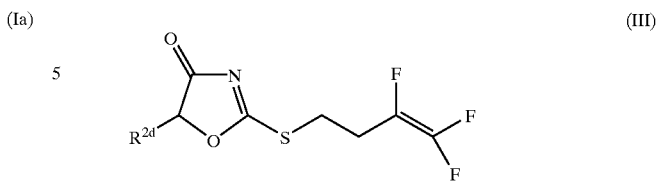

(III)

wherein
$R^{2d}$ represents hydrogen or alkyl,
are reacted with a halogenating agent in the presence of inert solvents, and, if appropriate, in the presence of an organic base.
Preparation Process f)
Compounds of the formula (I)
wherein
$R^1$ represents alkylsulfonyloxy,
$R^2$ represents hydrogen or alkyl and
n represents 0
are obtained when compounds of the aforementioned formula (III) are reacted with compounds of the formula

$R^{1d}SO_2Cl$ (IV)

wherein
$R^{1d}$ represents alkyl
in the presence of inert solvents, and if appropriate, in the presence of an inorganic or organic base.
Preparation Process g)
Compounds of the formula (I)
wherein
$R^1$ represents alkyl,
$R^2$ represents alkoxycarbonyl and
n represents 0
are obtained when compounds of the formula (IV)

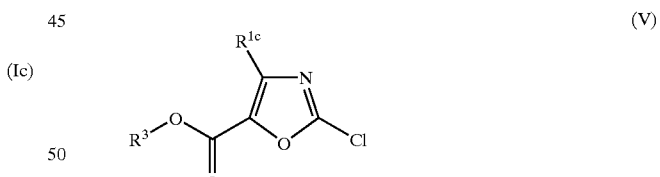

(V)

wherein
$R^{1c}$ is as defined above, and
$R^3$ represents alkyl,
are reacted with thiourea and the products are then reacted with 4-bromo-1,1,2-trifluoro-1-butene in the presence of inert solvents.
Preparation Process h)
Compounds of the formula (I)
wherein
$R^1$ represents hydrogen,
$R^2$ represents alkoxyalkyl and
n represents 0 are obtained when compounds of the formula (Id)

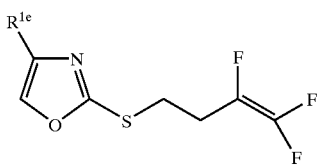
(Id)

wherein
$R^{1e}$ represents hydrogen,
are reacted with compounds of the formula (VI)

$$R^4—Br \quad (VI)$$

wherein
$R^4$ represents alkoxyalkyl,
in the presence of inert solvents.

The compounds of the formula (I) of the present invention exhibit strong nematicidal activity and show good compatibility with various crops.

The compounds of the formula (I) according to the present invention surprisingly show a very outstanding nematicidal activity compared with the compounds described in the aforementioned literature which are similar to the compounds of the present invention.

In the present specification "halogen" represents fluoro, chloro, bromo or iodo, preferably represents fluoro, chloro or bromo, and particularly preferably represents chloro or bromo.

"Alkyl" and each alkyl part of "alkoxy", "alkylthio", "alkylcarbonyloxy", "alkylsulfonyloxy" and "alkoxycarbonyl" represents a straight-chain or branched-chain alkyl such as methyl, ethyl, n- or i-propyl, n-, i-, s- or -t-butyl, n-pentyl, n-hexyl, n-heptyl, n-octyl, preferably represents methyl, ethyl, n- or i-propyl, n-, i-, s-, or t-butyl, n-pentyl or n-hexyl and particularly preferably represents methyl, ethyl, n- or i-propyl or n-, i-, s-, or t-butyl.

"Haloalkyl" and each haloalkyl part of "haloalkylcarbonyloxy", "haloalkoxy" and "haloalkylthio" represents alkyl substituted with at least one halogen, preferably represents $C_{1-4}$ alkyl substituted with one or a plurality of halogen, and particularly preferably represents methyl, ethyl or n- or i-propyl substituted with one or a plurality of fluoro, chloro or bromo. "Haloalkyl" preferably represents chloromethyl, bromomethyl or trifluoromethyl.

Very particular emphasis is given to the group of the compounds of the formula (I) wherein
$R^1$ represents hydrogen, halogen, represents methyl, ethyl, n- or i-propyl, n-, i-, s- or t-butyl, n-pentyl or n-hexyl, each of which may be substituted with halogen, hydroxy, methoxy, ethoxy, n- or i-propoxy, methylthio, ethylthio, n- or i-propylthio, methylcarbonyloxy, ethylcarbonyloxy, n- or i-propylcarbonyloxy, trifluoromethylcarbonyloxy or cyano, or represents methylsulfonyloxy, ethylsulfonyloxy, n- or i-propylsulfonyloxy, n-, i-, s- or t-butylsulfonyloxy or represents phenyl which may be substituted with halogen, methyl, trifluoromethyl, methoxy, methylthio, methylsulfonyl, trifluoromethoxy, trifluoromethylthio, phenyl, phenoxy, cyano or nitro,
$R^2$ represents hydrogen, halogen, methyl, ethyl, n- or i-propyl, n-, i-, s-, or t-butyl, n-pentyl or n-hexyl each of which may be substituted with methoxy, ethoxy, n- or i-propoxy or halogen or represents methoxycarbonyl, ethoxycarbonyl, n- or i-propoxycarbonyl or n-, i-, s-, or t-butoxycarbonyl, and
n represents 0, 1 or 2.

However, if $R^1$ represents methyl, ethyl, n- or i-propyl, n-, i-, s- or t-butyl, n-pentyl or n-hexyl, $R^2$ does not represent halogen.

Very particular preference is furthermore given to the group of compounds of the formula (I), wherein
$R^1$ represents hydrogen, fluoro, chloro, bromo, represents methyl, ethyl, n- or i-propyl, n-, i-, s- or t-butyl, each of which may be substituted with fluoro, chloro, bromo, hydroxy, methoxy, ethoxy, n- or i-propoxy, methylthio, ethylthio, n- or i-propylthio, trifluoromethylcarbonyloxy or cyano, or represents methylsulfonyloxy or ethylsulfonyloxy, or represents phenyl which may be substituted with fluoro, chloro, bromo, methyl, trifluoromethyl, methoxy, methylthio, methylsulfonyl, trifluoromethoxy, trifluoromethylthio, phenyl, phenoxy, cyano or nitro,
$R^2$ represents hydrogen, fluoro, chloro, bromo, represents methyl, ethyl, n- or i-propyl or n-, i-, s- or t-butyl each of which may be substituted with methoxy, ethoxy, n- or i-propoxy or bromo or represents methoxycarbonyl, ethoxycarbonyl or n- or i-propoxycarbonyl, and
n represents 0, 1 or 2.

However, if $R^1$ represents methyl, ethyl, n- or i-propyl or n-, i-, s- or t-butyl, $R^2$ does not represent fluoro, chloro or bromo.

The aforementioned preparation process a) can be represented by the following reaction scheme if, for example, 2-mercaptooxazole and 4-bromo-1,1,2-trifluoro-1-butene are used as starting materials.

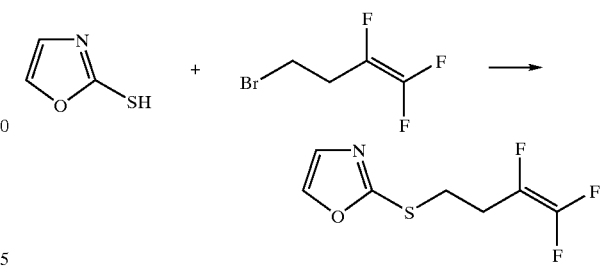

The aforementioned preparation process b) can be represented by the following reaction scheme, if, for example, 2-(3,4,4-trifluoro-3-butenylthio)oxazole is used as starting material and m-chloroperbenzoic acid is used as oxidizing agent.

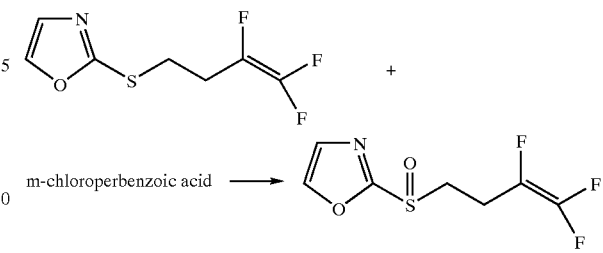

The aforementioned preparation process c) can be represented by the following reaction scheme, if, for example, 2-(3,4,4-trifluoro-3-butenylthio)oxazole is used as starting material and sulfuryl chloride is used as halogenating agent.

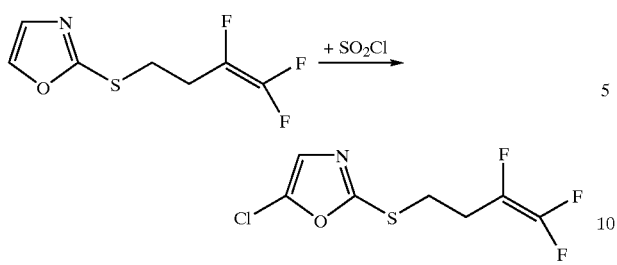

The aforementioned preparation process d) can be represented by the following reaction scheme, if, for example, 4-methyl-2-(3,4,4-trifluoro-3-butenylthio)oxazole is used as starting material and N-chlorosuccinimide is used as halogenating agent.

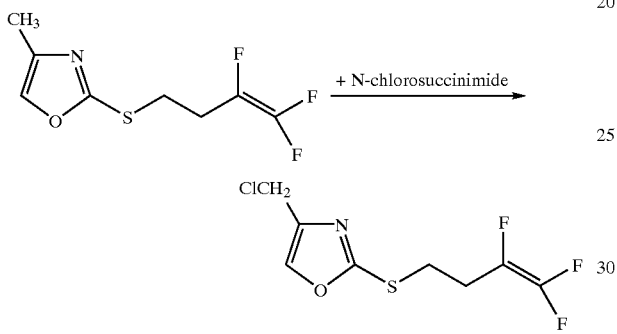

The aforementioned preparation process e) can be represented by the following reaction scheme, if, for example, 2-(3,4,4-trifluoro-3-butenylthio)oxazolidin-4-one is used as starting material and phosphorus oxychloride is used as halogenating agent.

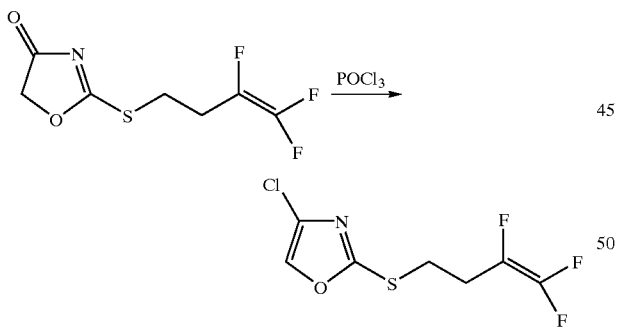

The aforementioned preparation process f) can be represented by the following reaction scheme, if, for example, 2-(3,4,4-trifluoro-3-butenylthio)oxazolidin-4-one and methanesulfonic chloride are used as starting materials.

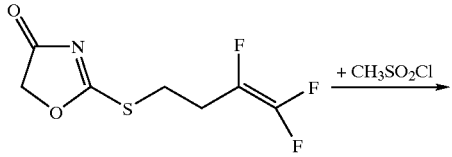

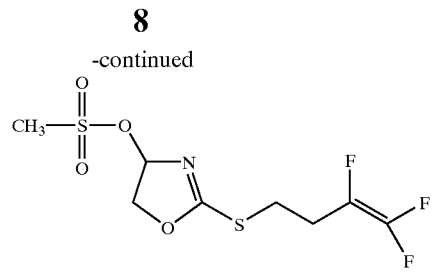

The aforementioned preparation process g) can be represented by the following reaction scheme, if, for example, 2-chloro-5-methoxycarbonyl-4-methyloxazole, thiourea and 4-bromo-1,1,2-trifluoro-1-butene are used as starting materials.

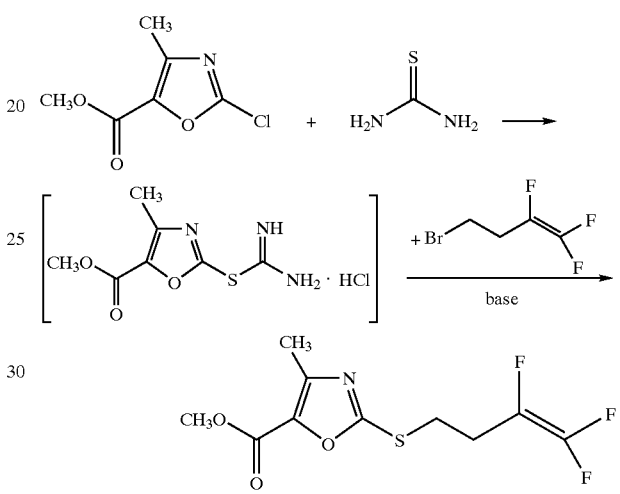

The aforementioned preparation process h) can be represented by the following reaction scheme, if, for example, 2-(3,4,4-trifluoro-3-butenylthio)oxazole and bromomethyl methyl ether are used as starting materials:

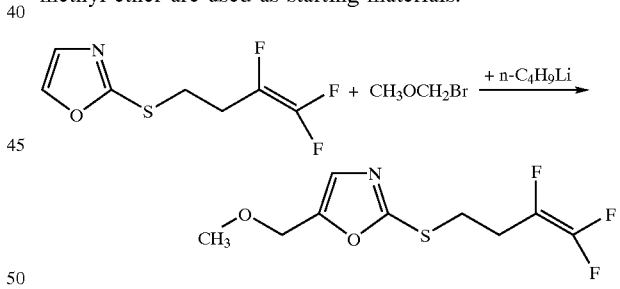

The compounds of the formula (II), used as starting material in the aforementioned preparation process a) include the known compounds described in the literature, for example in J. Org. Chem., (1988), 53 (5), 1113–1114; Collect. Czech. Chem. Commun. (1983), 48 (12), 3421–3425; Can. J. Chem., (1972), 50 (18), 3082–3083 etc.

As specific examples of the compounds of the formula (II) there can be mentioned, 2-mercaptooxazole,
2-mercapto-4-methyloxazole,
4-ethyl-2-mercaptooxazole,
2-mercapto-5-methyloxazole,
5-ethyl-2-mercaptooxazole,
2-mercapto-5-n-propyloxazole,
2-mercapto-4-n-propyloxazole, 2-mercapto-4-iso-propyloxazole,
2-mercapto-4-tert-butyloxazole,
2-mercapto-4,5-dimethyloxazole,
2-mercapto-4-phenyloxazole and so on.

4-Bromo-1,1,2-trifluoro-1-butene, used as starting material in the aforementioned preparation process a), is a known compound described in the document WO 86/07590.

The compounds of the formula (Ia), used as starting material in the aforementioned preparation process b), correspond to the compounds of formula (I) if n represents 0 and can be synthesized, for example, according to the aforementioned preparation process a).

As oxidizing agent used for the oxidation of the compounds of the above-mentioned formula (Ia) in the preparation process b) there can be mentioned those which are used usually in the field of organic chemistry, for example, hydrogen peroxide water, m-chloroperbenzoic acid, peracetic acid, perbenzoic acid, magnesium monoperoxyphthalate, potassium peroxymonosulfate and so on.

The compounds of the formula (Ib) and the formula (Ic), used as starting materials in the aforementioned preparation process c) and preparation d), respectively, are generally described by the formula (I) of the present invention, wherein n represents 0. They can be synthesized, for example, according to the aforementioned preparation process a).

As halogenating agent, which can be reacted with the compounds of the formula (Ib) and the formula (Ic) in the preparation process c) and preparation d), respectively, there can be mentioned those which are used usually in the field of organic chemistry, for example, sulfuryl chloride, N-chlorosuccinimide, N-bromosuccinimide, trichloroisocyanuric acid, potassium fluoride, chlorine gas, bromine, iodine and so on.

The compounds of the formula (III) used as starting materials in the aforementioned preparation process e) and preparation f) are novel compounds which were not described in the literature before. They can be prepared, for example, according to the following process i).

Preparation Process i)

Compounds of the formula (III) are obtained when compounds of the formula (VII)

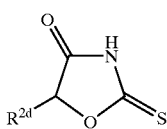

(VII)

wherein
$R^{2d}$ is as defined before,
are reacted with 4-bromo-1,1,2-trifluoro-1-butene in the presence of an inert solvent, and, if appropriate, in the presence of an acid binder.

The compounds of the above-mentioned formula (VII) include known compounds and can be synthesized, for example, according to the process described in Ukrain. Khim. Zhur., 16, 545–551 (1950).

As specific examples of the compounds of the aforementioned formula (III) there can be mentioned, for example, 2-(3,4,4-trifluoro-3-butenylthio)oxazolidin-4-one,
5-methyl-2-(3,4,4-trifluoro-3-butenylthio)oxazolidin-4-one and so on.

As halogenating agents, which can be reacted with the compounds of the aforementioned formula (III) in the preparation process e) there can be mentioned phosphorus oxychloride, phosphorus oxybromide, phosphorus pentachloride and so on.

The compounds of the aforementioned formula (IV), which are needed in the preparation process f), are well known in the field of organic chemistry. Specific examples which can be mentioned are methanesulfonic chloride, ethanesulfonic chloride etc.

The compounds of the formula (V) used as starting materials in the aforementioned preparation process g), are known compounds and can be prepared, for example, according to the process described in document WO 95/24403.

Specific examples of the compounds of the aforementioned formula (V) which can be mentioned are 2-chloro-5-methoxycarbonyl-4-methyloxazole, 2-chloro-5-ethoxycarbonyl-4-methyloxazole etc.

The compounds of the formula (Id) used as starting materials in the preparation process h) are generally described by the formula (I) of the present invention and can be synthesized, for example, according to the aforementioned preparation process a). Further, the compounds of the formula (VI), which are needed in the preparation process h), are well known compounds in the field of organic chemistry. Specific examples which can be mentioned are bromomethyl methyl ether, bromomethyl ethyl ether etc.

The reaction of the preparation process a) can be conducted in the presence of an adequate diluent. Examples of the diluents which can be used here are aliphatic, alicyclic and aromatic hydrocarbons, such as hexane, cyclohexane, petroleum ether, ligroine, benzene, toluene or xylene; ethers, such as, diethyl ether, methyl ethyl ether, di-isopropyl ether, dibutyl ether, propylene oxide, dioxane or tetrahydrofuran; ketones, such as acetone, methyl ethyl ketone or methyl isobutyl ketone; nitriles, such as acetonitrile, propionitrile or acrylonitrile; acid amides, such as, dimethylformamide, dimethylacetamide or N-methylpyrrolidone.

The reaction of the preparation process (a) can be conducted in the presence of an acid binder. Acid binders which can be used are, for example, hydroxides, carbonates and alcoholates etc. of alkali metals, tertiary amines, such as, triethylamine, diethylaniline, pyridine, 4-dimethylaminopyridine, 1,4-diazabicyclo[2,2,2]octane (DABCO) or 1,8-diazabicyclo[5,4,0]undec-7-ene (DBU).

The reaction of the preparation process a) can be conducted in a substantially wide range of temperature. In general, the processes are carried out at temperatures between 0° C. and 150° C., preferably between 20° C. and 100° C. Although said reaction is generally carried out under normal pressure, it can be optionally carried out under elevated pressure or under reduced pressure.

When carrying out the preparation process a), the compounds of the corresponding formula (I) can be obtained by reacting, for example, 0.7–1.5 moles of 4-bromo-1,1,2-trifluoro-1-butene with 1 mole of the compounds of the formula (II) in a diluent, for example, acetonitrile in the presence of 1–1.3 moles of an acid binder, for example, potassium carbonate, under reflux by heating.

Among the compounds of the formula (I) of the present invention which can be prepared by the preparation process a), the compounds the formula (I) wherein $R^1$ represents hydroxymethyl, alkoxymethyl, halogenomethyl, alkylcarbonyloxy, alkylthiomethyl or cyanomethyl, $R^2$ represents hydrogen and n represents 0, can be also synthesized according to other processes described in Synthesis Examples 10–14 below.

The reaction of the preparation process b) can be carried out in the presence of an adequate diluent. Examples of the diluents which can be used are aliphatic, alicyclic and aromatic hydrocarbons which may be optionally chlorinated, such as, hexane, cyclohexane, petroleum ether, ligroine, benzene, toluene, xylene, methylene chloride, chloroform, carbon tetrachloride, ethylene chloride or chlorobenzene; ethers, such as, diethyl ether, methyl ethyl ether, di-isopropyl ether, dibutyl ether, propylene oxide, dioxane or tetrahydrofuran; alcohols, such as, methanol, ethanol, isopropanol, butanol or ethylene glycol; esters, such as, ethyl acetate or amyl acetate; acid amides, such as, dimethylformamide, dimethylacetamide or N-methylpyrrolidone; carboxylic acids, such as, formic acid or acetic acid.

The reaction of the preparation process b) can be conducted in a substantially wide range of temperatures. In general, the processes are carried out at temperatures between −20° C. and 100° C., preferably between 0° C. and 80° C. Although said reaction is generally carried out under normal pressure, it can be optionally carried out under elevated pressure or under reduced pressure.

When carrying out the preparation process b), the compounds of the corresponding formula (I) can be obtained by reacting, for example, 0.8–3 moles of m-chloroperbenzoic acid with 1 mole of the compounds of the formula (Ia) in a diluent, for example, methylene chloride, at room temperature.

The reaction of the preparation processes c) and d) can be carried out in the presence of an adequate diluent. Examples of the diluents which can be used are aliphatic, alicyclic and aromatic hydrocarbons which may be optionally chlorinated, such as, hexane, cyclohexane, petroleum ether, ligroine, benzene, toluene, xylene, methylene chloride, chloroform, carbon tetrachloride, ethylene chloride or chlorobenzene; ethers, such as, diethyl ether, methyl ethyl ether, di-isopropyl ether, dibutyl ether, propylene oxide, dioxane or tetrahydrofuran; acid amides, such as, dimethylformamide, dimethylacetamide or N-methylpyrrolidone; sulfones and sulfoxides, such as, dimethyl sulfoxide or sulfolane.

The reaction of the preparation processes c) and d) can be conducted in a substantially wide range of temperatures. In general, the processes are carried out at temperatures between −20° C. and 200° C., preferably between 0° C. and 150° C. Although said reaction is generally carried out under normal pressure, it can be optionally carried out under elevated pressure or under reduced pressure.

When carrying out the preparation processes c) and d), the compounds of the corresponding formula (I) can be obtained by reacting e.g. 1–4 moles of N-chlorosuccinimide with 1 mole of the compounds of the formula (Ib) in a diluent, such as, carbon tetrachloride, under reflux by heating.

The reaction of the preparation process e) can be carried out in the presence of an adequate diluent. Examples of the diluent which can be used are hydrocarbons including halogenated hydrocarbons, ethers, nitrites and acid amides according to the list of diluents mentioned in the aforementioned preparation process b).

The reaction of the preparation process (e) can be carried out in the presence of an organic base. Organic bases which can be used are, for example, triethylamine, 1,1,4,4-tetramethylethylenediamine (TMEDA), N,N-dimethylaniline or pyridine.

The reaction of the preparation process e) can be carried out in a substantially wide range of temperatures. In general, the processes are carried out at temperatures between 0° C. and 200° C., preferably between 20° C. and 120° C. Although said reaction is generally carried out under normal pressure, it can be optionally carried out under elevated pressure or under reduced pressure.

When carrying out the preparation process e), the compounds of the corresponding formula (I) can be obtained by reacting, for example, 1–5 moles of a halogenating agent to 1 mole of the compounds of the formula (III) in the presence of pyridine.

The reaction of the preparation process f) can be carried out in the presence of an adequate diluent. Examples of the diluents which can be used are the same diluents as mentioned in the aforementioned preparation process e) and, in addition, there can be mentioned alkylsulfonyl chlorides, for example, methanesulfonyl chloride, ethanesulfonyl chloride or isopropylsulfonyl chloride.

Further, the reaction of the preparation process (f) can be carried out in the presence of inorganic bases and organic bases. Organic bases which can be used are the same ones as exemplified in the aforementioned preparation process e). Inorganic bases which can be used are, for example, sodium carbonate or potassium carbonate.

The reaction of the preparation process f) can be carried out in a substantially wide range of temperature. In general, the processes are carried out at temperatures between −20° C. and 150° C., preferably between 0° C. and 130° C. Although said reaction is generally carried out under normal pressure, it can be optionally carried out under elevated pressure or under reduced pressure.

When carrying out the preparation process f), the compounds of the corresponding formula (I) can be obtained by reacting, for example, 1–3 moles of a compound of the formula (IV) to 1 mole of the compounds of the formula (III) with an organic base, for example triethylamine, in the presence of a diluent, for example tetrahydrofuran.

The reaction of the preparation process g) can be carried out in the presence of an adequate diluent. Diluents which can be used are the same diluents as mentioned in the aforementioned preparation process a) and, in addition, alcohols, for example, methanol, ethanol or isopropanol.

The reaction of the preparation process g) can be carried out in a substantially wide range of temperature. In general, the processes are carried out at temperatures between 0° C. and 150° C., preferably between 20° C. and 120° C. Although said reaction is generally carried out under normal pressure, it can be optionally carried out under elevated pressure or under reduced pressure.

When carrying out the preparation process g), the compounds of the corresponding formula (I) can be obtained by reacting, for example, 1–1.5 moles of thiourea to 1 mole of the compounds of the formula (V) in a diluent, for example, ethanol and then reacting with 1–1.5 moles of 4-bromo-1,1,2-trifluoro-1-butene.

The reaction of the preparation process h) can be carried out in the presence of an adequate diluent. Diluents which can be used are, for example, the ethers exemplified before.

The reaction of the preparation process h) can be carried out in a substantially wide range of temperature. In general, the processes are carried out at temperatures between 100° C. and 150° C., preferably between −78° C. and 100° C. Although said reaction is generally carried out under normal pressure, it can be optionally carried out under elevated pressure or under reduced pressure.

When carrying out the preparation process h), the compounds of the corresponding formula (I) can be obtained by reacting, for example, 1–1.5 moles of the compounds of the formula (VI) to 1 mole of the compound of the formula (Id) in a diluent, for example, diethyl ether, in the presence of n-butyl lithium.

The reaction of the preparation process i) can be carried out in the presence of an adequate diluent. Diluents which can be used are the same diluents as mentioned in the aforementioned preparation process a).

The reaction of the preparation process (i) can be carried out in the presence of the same acid binder as mentioned in the aforementioned preparation process a).

The reaction of the preparation process (i) can be carried out by applying the same reaction temperatures and pressures mentioned in the aforementioned preparation process a).

When carrying out the preparation process i), the compounds of the corresponding formula (III) can be obtained by reacting, for example, 0.7–1.5 moles of 4-bromo-1,1,2-trifluoro-1-butene to 1 mole of the compounds of the formula (VII) in a diluent, for example, tetrahydrofuran, in the presence of 1–1.3 moles of triethylamine.

The compounds of the formula (I) of the present invention show a strong ability to control nematodes. They can, therefore, be efficiently used as nematicidal agents.

Furthermore, the compounds of the formula (I) of the present invention show no phytotoxicity against crops and at the same time exhibit the ability to specifically control harmful nematodes.

Examples of nematodes against which the active compounds of the formula (I) of the present invention can be applied are, for example, Pratylenchus spp., *Globodera rostochiensis* Wollenweber, Heterodera spp., such as, *Heterodera glycines* Ichinohe, Meloidogyne spp., *Aphelenchoides basseyi* Christie, *Bursaphelenchus Xylophilis, Radopholus similis, Ditylenchus dipsaci, Tylenchulus semipenetrans* etc. However, the nematodes which can be controlled by said compounds are not limited to the above list.

The active compounds of the present invention can also be used as mixtures with other active compounds, such as, insecticides, bactericides, miticides, fungicides etc. in the form of their commercially useful formulation or in the application form prepared from those formulations. Possible components for the mixtures are insecticides, for example organophosphorus agents, carbamate agents, carboxylate type chemicals, chlorinated hydrocarbon type chemicals or chloronicotinyl type chemicals, insecticidal substances produced by microbes.

Further, the active compounds of the present invention can also be used as mixtures with synergists in such formulations and application forms as can be mentioned as commercially useful. A synergist itself must not be active, but enhances the action of the active compound.

The content of the active compounds of the present invention in a commercially useful formulation or application form can be varied in a wide range. The application concentration of the active compounds of the formula (I) of the present invention can be in the range of generally 0.000001–100% by weight, preferably 0.00001–1% by weight.

The active compounds of the present invention can be converted into the customary formulations, such as, solutions, emulsions, wettable powders, water dispersible granules, suspensions, powders, foaming agents, pastes, granules, active compound-impregnated natural and synthetic substances, microcapsules, fumigants etc.

These formulations can be prepared according to per se known methods, for example by mixing the active compounds with extenders, namely liquid solvents, liquefied gas and/or solid diluents or carriers, and optionally with surfactants, namely emulsifiers and/or dispersants and/or foam formers. When water is used as extender, it is also possible to use, for example, organic solvents as auxiliary solvents.

Liquid diluents or carriers which can be used are, for example, aromatic hydrocarbons, such as, xylene, toluene or alkylnaphthalene, chlorinated aromatic or chlorinated aliphatic hydrocarbons, such as, chlorobenzenes, ethylene chlorides or methylene chloride, aliphatic hydrocarbons such as cyclohexane or paraffins, such as, mineral oil fractions, alcohols, such as, butanol, glycols and their ethers or esters, ketones, such as, acetone, methyl ethyl ketone, methyl isobutyl ketone or cyclohexanone, strongly polar solvents, such as, dimethylformamide or dimethyl sulphoxide, water and so on.

Liquefied gas diluents or carriers are liquefied substances which are gases at normal temperature and pressure. Examples are aerosol propellants such as butane, propane, nitrogen gas, carbon dioxide and halogenated hydrocarbons.

Solid diluents which can be used are, for example, ground natural minerals such as kaolin, clay, talc, chalk, quartz, attapulgite, montmorillonite or diatomaceous earth, ground synthetic minerals such as highly dispersed silicic acid, alumina or silicates and so on.

Solid carriers for granules which can be used are for, example, crushed and fractionated rocks, such as, calcite, marble, pumice, sepiolite or dolomite synthetic granules of inorganic and organic meals, particles of organic materials, such as, sawdust, coconut shells, maize cobs or tobacco stalks and so on.

Emulsifiers and/or foam-forming agents which can be used are, for example, nonionic and anionic emulsifiers, such as, polyoxyethylene fatty acid esters or polyoxyethylene fatty acid alcohol ethers, such as, alkylaryl polyglycol ethers, alkylsulphonates, alkylsulphates or arylsulphonates, albumin hydrolysis products and so on.

Dispersants include, for example, ligninsulphite waste liquor and methyl cellulose.

Tackifiers may also be used in formulations, such as, powders, granules or emulsions. Tackifiers which can be used are, for example, carboxymethyl cellulose, natural and synthetic polymers, such as, gum arabic, polyvinyl alcohol or polyvinyl acetate.

Colorants may also be used. Colorants which can be used are, for example, inorganic pigments such as iron oxide, titanium oxide or Prussian Blue, organic dyestuffs, such as, alizarin dyestuffs, azo dyestuffs or metal phthalocyanine dyestuffs, and further trace nutrients, such as, salts of metals such as iron, manganese, boron, copper, cobalt, molybdenum or zinc.

Said formulations generally comprise the aforementioned active components in a range of between 0.1–95% by weight, preferably between 0.5–90% by weight.

The preparation and use of the compounds of the present invention will be described more specifically in the following examples. However, the present invention should not be restricted to them in any way. "Parts" means "parts by weight" unless specified.

EXAMPLES

Preparation Examples

Example 1

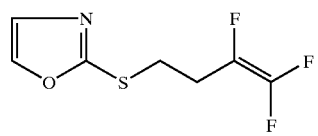

7.5 g of 4-bromo-1,1,2-trifluoro-1-butene and 7.0 g of potassium carbonate were added to 50 ml of acetonitrile, 3.8 g of 2-mercaptooxazole, and refluxed for 5 hours by heating. After cooling the reaction mixture to room temperature, solid substance was filtered by suction and the filtrate was distilled off under reduced pressure. The residue was purified by column chromatography (eluent: hexane:dichloromethane=1:1) to obtain 6.5 g of 2-(3,4,4-trifluoro-3-butenylthio)oxazole as colorless oil (yield 82.7%, $n^{20}_D$=1.4631).

Example 2

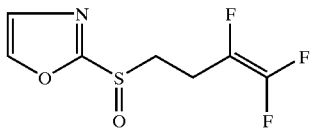

1.0 g of 2-(3,4,4-trifluoro-3-butenylthio)oxazole and 1.5 g of m-chloroperbenzoic acid (purity about 70%) were added to 50 ml of dichloromethane and stirred at room temperature for 20 hours. The reaction mixture was washed with 50 ml of 1N aqueous solution of sodium hydroxide and dried with magnesium sulfate. After the solvent was distilled off under reduced pressure, the residue was purified by column chromatography (eluent: ethyl acetate:dichloromethane=1:4) to obtain 1.0 g of 2-(3,4,4-trifluoro-3-butenylsulfinyl)oxazole as colorless oil (yield 92.9%, $n^{20}_D$=1.4820).

Example 3

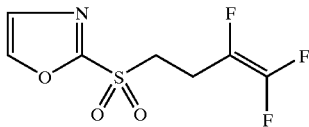

1.0 g of 2-(3,4,4-trifluoro-3-butenylthio)oxazole and 3.0 g of m-chloroperbenzoic acid (purity about 70%) were added to 50 ml of dichloromethane and stirred at room temperature for 20 hours. The reaction mixture was washed with 50 ml of 1N aqueous solution of sodium hydroxide and dried with magnesium sulfate. After the solvent was distilled off under reduced pressure, the residue was purified by column chromatography (eluent: dichloromethane) to obtain 0.8 g of 2-(3,4,4-trifluoro-3-butenylsulfonyl)oxazole as colorless oil (yield 69.4%, $n^{20}_D$=1.4705).

Example 4

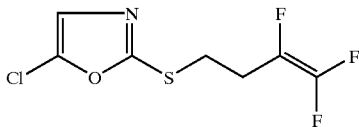

4.0 g of 2-(3,4,4-trifluoro-3-butenylthio)oxazole was added to 40 ml of DMF (dehydrated) to which a mixture of 10 ml of chloroform and 2.6 g of sulfuryl chloride was added dropwise at 50 in 1 hour. After the reaction mixture was stirred at 50° C. for 3 hours, a mixture of 5 ml of chloroform and 0.8 g of sulfuryl chloride was further added dropwise in 15 minutes. After stirring at 50° C. for 15 hours, the reaction mixture was cooled to room temperature, poured into 200 ml of ice water and extracted with 100 ml of hexane. The aqueous layer was neutralized with 1N aqueous solution of sodium hydroxide and further extracted with 100 ml of hexane. The extracted hexane layers were put together, washed with 200 ml of saturated common salt water and dried with magnesium sulfate. After the solvent was distilled off under reduced pressure, the residue was purified by column chromatography (eluent: hexane:dichloromethane= 1:1) to obtain 2.4 g of 5-chloro-2-(3,4,4-trifluoro-3-butenylthio)oxazole as colorless oil (yield 51.5%, $n^{20}_D$= 1.4830).

Example 5

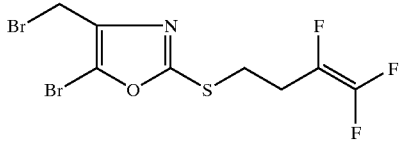

2.2 g of 4-methyl-2-(3,4,4-trifluoro-3-butenylthio) oxazole was dissolved in 40 ml of dichloromethane and 3.4 g of N-bromosuccinimide were added and stirred at room temperature for 5 hours. After the solvent was distilled off under reduced pressure, the residue was purified by column chromatography (eluent: hexane:ethyl acetate=93:7) to obtain 2.4 g of 5-bromo-4-bromomethyl-2-(3,4,4-trifluoro-3-butenylthio)oxazole (yield 63%). $n^{20}_D$=1.4963.

Example 6

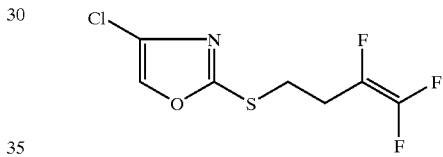

2 g of phosphorus oxychloride were added dropwise to a mixture of 1 g of 2-(3,4,4-trifluoro-3-butenylthio) oxazolidin-4-one and 0.35 g of pyridine under ice cooling and stirred at 70–80° C. for 3 hours. After addition of ice water to the reaction mixture and stirring for 30 minutes, the mixture was extractred with dichloromethane. The extracted layer was washed with water, dried with anhydrous sodium sulfate and the solvent was distilled off under reduced pressure. The residue was purified by column chromatography (eluent: dichloromethane) to obtain 0.7 g of 4-chloro-2-(3,4,4-trifluoro-3-butenylthio)oxazole (yield 65%). $n^{20}_D$= 1.4813.

Example 7

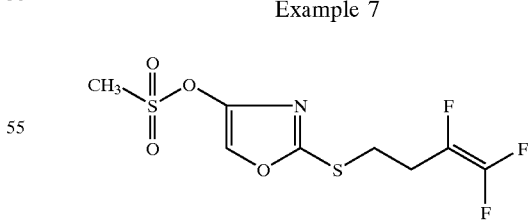

1 g of 2-(3,4,4-trifluoro-3-butenylthio)oxazolidin-4-one and 0.9 g of triethylamine were dissloved in 30 ml of tetrahydrofuran, to which 0.56 g of methanesulfonic chloride was added dropwise under ice cooling and stirred at 50° C. for 8 hours. After distilling off the solvent under reduced pressure, the residue was dissolved in ether. After washing with 1N hydrochloric acid and water, it was dried with anhydrous sodium sulfate and the solvent was distilled off under reduced pressure. The residue was purified by column chromatography (eluent: hexane:dichloromethane=1:1) to obtain 0.25 g of 4-methylsulfonyloxy-2-(3,4,4-trifluoro-3-butenylthio)oxazole (yield 19%). $n^{20}_D$=1.4830.

Example 8

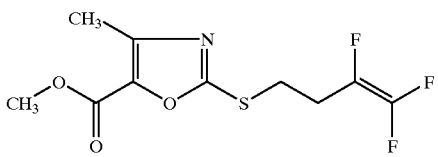

2.1 g of 2-chloro-5-methoxycarbonyl-4-methyloxazole and 1.1 g of thiourea were dissloved in 55 ml of ethanol and refluxed for 8 hours. After cooling, the solvent was distilled off under reduced pressure. The residue was dissolved in 55 ml of acetone, to which 2.5 g of 4-bromo-1,1,2-trifluoro-1-butene and 2.4 g of potassium carbonate were added, stirred at room temperature for 18 hours and the solvent was distilled off under reduced pressure. After addition of 50 ml of water to the residue and extraction with ether, the ether layer was washed with water and dried with anhydrous sodium sulfate. After the solvent was distilled off under reduced pressure, the residue was treated by silica gel column chromatography to obtain 3.1 g of 5-methoxycarbonyl-4-methyl-2-(3,4,4-trifluoro-3-butenylthio)oxazole. $n^{20}_D$=1.4972.

Example 9

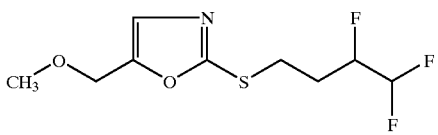

10.40 ml of n-butyl lithium (1.6 M n-hexane solution) were slowly added dropwise to a solution of 3.14 g of 2-(3,4,4-trifluoro-3-butenylthio)oxazole in 40 ml of ether at −70° C. After stirring for 1 hour, a solution of 2.06 g bromomethyl methyl ether in 10 ml ether was added dropwise. After bringing the mixture back to room temperature and stirring for 1 hour, 50 ml of saturated solution of ammonium chloride was added to separate it into an ether layer and an aqueous layer. The aqueous layer was further extracted with ether and together with the separated ether layer it was washed with a saturated sodium chloride water and dried with anhydrous magnesium sulfate. After the solvent was distilled off under reduced pressure, the residue was treated by column chromatography to obtain 0.5 g of 5-methoxymethyl-2-(3,4,4-trifluoro-3-butenylthio)oxazole (yield 13%). $n^{20}_D$=1.4705.

Example 10

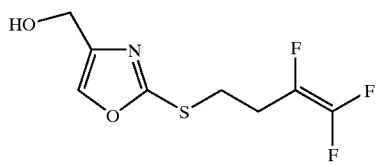

7.5 g of 3,8-dioxa-1,6-diazaspiro[4,4]nona-1,6-diene-2,7-dithiol, 7.5 g of 4-bromo-1,1,2-trifluoro-1-butene and 7.0 g of potassium carbonate were added to 200 ml of acetonitrile and refluxed for 5 hours. The reaction mixture was cooled to room temperature and filtered by sucction and the filtrate was distilled under reduced pressure. The residue was purified by column chromatography (eluent: ethyl acetate:dichloromethane=1:4) to obtain 7.0 g of 4-hydroxymethyl-2-(3,4,4-trifluoro-3-butenylthio)oxazole as colorless oil (yield 74.2%). $n^{20}_D$=1.4910.

Example 11

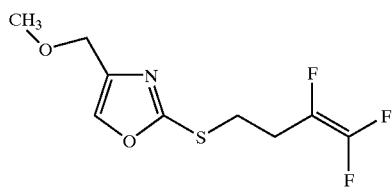

A solution of 2.7 g of 4-hydroxymethyl-2-(3,4,4-trifluoro-3-butenylthio)oxazole in 50 ml of tetrahydrofuran (dehydrated) was added dropwise to a suspension of 0.5 g NaH (purity about 60%) in 20 ml of tetrahydrofuran (dehydrated) at 0° C. After stirring the mixture at room temperature for 1 hour, a solution of 2.0 g of methyl iodide in 20 ml of tetrahydrofuran (dehydrated) was added at 0° C. and further stirred at room temperature for 1 hour. The reaction mixture was poured into a mixed solution of 200 g ice and 2N hydrochloric acid. After extraction with 100 ml of dichloromethane, the solution was washed with water and dried with anhydrous magnesium sulfate. After the solvent was distilled off under reduced pressure, the residue was purified by column chromatography (eluent: dichloromethane) to obtain 1.5 g of 4-methoxymethyl-2-(3,4,4-trifluoro-3-butenylthio)oxazole as colorless oil (yield 52.5%). $n^{20}_D$=1.4710.

Example 12

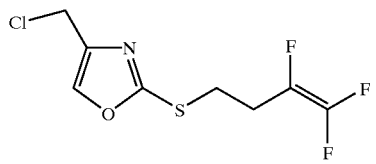

6.8 g of 4-hydroxymethyl-2-(3,4,4-trifluoro-3-butenylthio)oxazole and 2.5 g of pyridine were dissolved in 30 ml of chloroform, to which a solution of 5.0 g of thionyl chloride in 10 ml of chloroform was added dropwise at 0° C. After the addition the mixture was refluxed for 10 hours. After cooling to room temperature, the solvent was distilled under reduced pressure. The residue was purified by column chromatography (eluent: hexane:dichloromethane=2:1) to obtain 5.7 g of 4-chloromethyl-2-(3,4,4-trifluoro-3-butenylthio)oxazole as colorless oil (yield 77.8%). $n^{20}_D$=1.4933.

Example 13

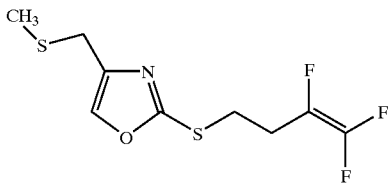

1.2 g of 4-chloromethyl-2-(3,4,4-trifluoro-3-butenylthio)oxazole, 0.5 g of sodium thiomethoxide and 0.1 g of sodium iodide were added to 20 ml of dimethylformamide (hehydrated) and stirred at 80° C. for 10 hours. After cooling, 200 ml of water were added to the reaction mixture and extracted with 100 ml of diethyl ether twice. The extracted diethyl ether layers were put together, washed with 200 ml of water, dried with magnesium sulfate and the solvent was distilled off under reduced pressure. The residue was purified by column chromatography (eluent: hexane:dichloromethane=2:1) to obtain 0.3 g of 4-methylthiomethyl-2-(3,4,4-trifluoro-3-butenylthio)oxazole as colorless oil (yield 23.9%). $n^{20}_D$=1.5099.

Example 14

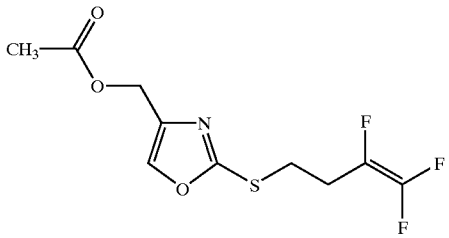

3 g of 4-hydroxymethyl-2-(3,4,4-trifluoro-3-butenylthio)oxazole and 1.5 g of triethylamine were dissolved in 50 ml of dichloromethane, to which a solution of 1 g of acetyl chloride in 20 ml of dichloromethane was added dropwise under ice cooling. After stirring at room temperature for 8 hours, the mixture was washed with water and dried with anhydrous sodium sulfate. After the solvent was distilled off under reduced pressure, the residue was treated by column chromatography to obtain 2.7 g of 4-acetoxymethyl-2-(3,4,4-trifluoro-3-butenylthio)oxazole (yield 76.5%). $n^{20}_D$=1.4752.

Example 15

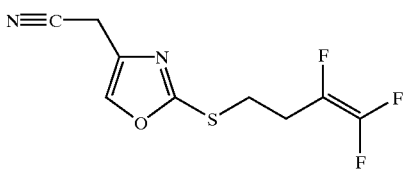

1.2 g of 4-chloromethyl-2-(3,4,4-trifluoro-3-butenylthio)oxazole, 1 g of potassium cyanide, 0.1 g of 18-crown-6-ether and 0.1 g of sodium iodide were added to 20 ml of dimethylformamide (dehydrated) and stirred at 100° C. for 20 hours. After cooling, 200 ml of water was added to the reaction mixture and extracted with 100 ml of diethyl ether twice. The extracted diethyl ether layers were put together, washed with 200 ml of water, dried with magnesium sulfate and the solvent was distilled off under reduced pressure. The residue was purified by column chromatography (eluent: hexane:dichloromethane=2:1) to obtain 0.3 g of 4-cyanomethyl-2-(3,4,4-trifluoro-3-butenylthio)oxazole as colorless oil (yield 15.6%). $n^{20}_D$=1.4844.

The compounds of the formula (I) of the present invention, synthesized by the similar manner to the processes described in the above-mentioned Synthesis Examples 1–9 are shown in Table 1. And the compounds of Synthesis Examples 1–15 are also shown in Table 1.

In Table 1, Me represents methyl, Et represents ethyl, n-Pr represents n-propyl, i-Pr represents isopropyl, n-Bu represents n-butyl, t-Bu represents t-butyl, n-Pen represents n-pentyl, n-Hexrepresents n-hexyl and Ph represents phenyl.

TABLE 1

| Compound No. | $R^1$ | $R^2$ | n | mp or $n^{20}_D$ |
|---|---|---|---|---|
| 1 | H | H | 0 | 1.4631 |
| 2 | H | H | 1 | 1.4820 |
| 3 | H | H | 2 | 1.4705 |
| 4 | H | Cl | 0 | 1.4830 |
| 5 | H | Cl | 1 | 1.4980 |
| 6 | H | Cl | 2 | 1.4805 |
| 7 | H | Br | 0 | 1.5029 |
| 8 | H | Br | 1 | 1.5110 |
| 9 | H | Br | 2 | |
| 10 | H | I | 0 | |
| 11 | H | I | 1 | |
| 12 | H | I | 2 | |
| 13 | H | Me | 0 | |
| 14 | H | Me | 1 | |
| 15 | H | Et | 0 | |
| 16 | Me | H | 0 | 1.4665 |
| 17 | Me | H | 1 | 1.4788 |
| 18 | Me | H | 2 | 1.4641 |
| 19 | Me | Me | 0 | 1.4702 |
| 20 | Me | Me | 1 | 1.4825 |
| 21 | Me | Me | 2 | 1.4683 |
| 22 | Me | Et | 0 | |
| 23 | Me | n-Pr | 0 | |
| 24 | Et | H | 0 | |
| 25 | Et | H | 1 | |
| 26 | Et | H | 2 | |
| 27 | n-Pr | H | 0 | |
| 28 | n-Pr | H | 1 | |
| 29 | i-Pr | H | 0 | |
| 30 | n-Bu | H | 0 | |
| 31 | n-Bu | H | 2 | |
| 32 | t-Bu | H | 0 | |
| 33 | n-Pen | H | 0 | |
| 34 | ClCH$_2$ | H | 0 | 1.4933 |
| 35 | ClCH$_2$ | Cl | 0 | |
| 36 | ClCH$_2$ | Cl | 1 | |
| 37 | ClCH$_2$ | Cl | 2 | |
| 38 | BrCH$_2$ | H | 0 | |
| 39 | BrCH$_2$ | Br | 0 | 1.4963 |
| 40 | BrCH$_2$ | Br | 2 | 1.4745 |
| 41 | BrCH$_2$ | BrCH$_2$ | 0 | |
| 42 | BrCH$_2$ | BrCH$_2$ | 1 | |

TABLE 1-continued

| Compound No. | R¹ | R² | n | mp or $n^{20}_D$ |
|---|---|---|---|---|
| 43 | BrCH₂ | BrCH₂ | 2 | |
| 44 | BrCH₂ | Me | 0 | |
| 45 | Me | BrCH₂ | 0 | |
| 46 | H | MeOCH₂ | 0 | 1.4705 |
| 47 | H | MeOCH₂ | 1 | 1.4812 |
| 48 | H | MeOCH₂ | 2 | |
| 49 | H | EtOCH₂ | 0 | |
| 50 | H | EtOCH₂ | 2 | |
| 51 | H | i-PrOCH₂ | 0 | |
| 52 | Cl | H | 0 | 1.4813 |
| 53 | Cl | H | 1 | |
| 54 | Cl | H | 2 | 1.4785 |
| 55 | Cl | Me | 0 | |
| 56 | Cl | Me | 1 | |
| 57 | Cl | Me | 2 | |
| 58 | Cl | Et | 0 | |
| 59 | Cl | Et | 1 | |
| 60 | Cl | Er | 2 | |
| 61 | Cl | n-Pr | 0 | |
| 62 | Cl | i-Pr | 0 | |
| 63 | Cl | Cl | 0 | |
| 64 | Br | H | 0 | 1.5012 |
| 65 | Br | H | 1 | 1.5226 |
| 66 | Br | H | 2 | |
| 67 | I | H | 0 | |
| 68 | I | H | 2 | |
| 69 | Me | MeOOC | 0 | 1.4972 |
| 70 | Me | MeOOC | 1 | |
| 71 | Me | MeOOC | 2 | 1.4710 |
| 72 | Me | EtOOC | 0 | |
| 73 | Me | EtOOC | 1 | |
| 74 | Me | n-PrOOC | 0 | |
| 75 | HOCH₂ | H | 0 | 1.4910 |
| 76 | HOCH₂ | H | 1 | |
| 77 | HOCH₂ | H | 2 | |
| 78 | MeOCH₂ | H | 0 | 1.4710 |
| 79 | MeOCH₂ | H | 1 | |
| 80 | MeOCH₂ | H | 2 | 1.4700 |
| 81 | EtOCH₂ | H | 0 | |
| 82 | EtOCH₂ | H | 1 | |
| 83 | EtOCH₂ | H | 2 | |
| 84 | n-PrOCH₂ | H | 0 | |
| 85 | i-PrOCH₂ | H | 0 | |
| 86 | MeSCH₂ | H | 0 | 1.5099 |
| 87 | MeSCH₂ | H | 1 | |
| 88 | MeSCH₂ | H | 2 | |
| 89 | EtSCH₂ | H | 0 | |
| 90 | EtSCH₂ | H | 1 | |
| 91 | EtSCH₂ | H | 2 | |
| 92 | n-PrSCH₂ | H | 0 | |
| 93 | i-PrSCH₂ | H | 0 | |
| 94 | MeCOOCH₂ | H | 0 | 1.4752 |
| 95 | MeCOOCH₂ | H | 1 | |
| 96 | MeCOOCH₂ | H | 2 | 1.4765 |
| 97 | EtCOOCH₂ | H | 0 | |
| 98 | EtCOOCH₂ | H | 1 | |
| 99 | EtCOOCH₂ | H | 2 | |
| 100 | n-PrCOOCH₂ | H | 0 | |
| 101 | i-PrCOOCH₂ | H | 0 | |
| 102 | CF₃COOCH₂ | H | 0 | 1.4430 |
| 103 | CF₃COOCH₂ | H | 1 | |
| 104 | CF₃COOCH₂ | H | 2 | 1.4388 |
| 105 | NCCH₂ | H | 0 | 1.4844 |
| 106 | NCCH₂ | H | 1 | |
| 107 | NCCH₂ | H | 2 | |
| 108 | Ph | H | 0 | 1.5455 |
| 109 | Ph | H | 1 | |
| 110 | Ph | H | 2 | 1.5368 |
| 111 | 2-F-Ph | H | 0 | |
| 112 | 4-Cl-Ph | H | 0 | |
| 113 | 4-Cl-Ph | H | 2 | |
| 114 | 3-Me-Ph | H | 0 | |
| 115 | 4-CF₃-Ph | H | 0 | |
| 116 | 4-MeO-Ph | H | 0 | |
| 117 | 4-MeS-Ph | H | 0 | |
| 118 | 4-MeSO₂-Ph | H | 2 | |
| 119 | 4-CF₃O-Ph | H | 0 | |
| 120 | 4-CF₃S-Ph | H | 0 | |
| 121 | 4-Ph-Ph | H | 0 | |
| 122 | 4-PhO-Ph | H | 0 | |
| 123 | 4-CN-Ph | H | 0 | |
| 124 | 4-NO₂-Ph | H | 0 | |
| 125 | 3,4-diMe-Ph | H | 0 | |
| 126 | 2,4-diCl-Ph | H | 0 | |
| 127 | MeSO₂O | H | 0 | 1.4830 |
| 128 | MeSO₂O | H | 1 | |
| 129 | MeSO₂O | H | 2 | |
| 130 | EtSO₂O | H | 0 | |
| 131 | EtSO₂O | H | 2 | |
| 132 | n-Hex | H | 0 | |
| 133 | H | n-Pr | 0 | |
| 134 | H | iso-Pr | 0 | |
| 135 | H | iso-Pr | 2 | |
| 136 | H | n-Bu | 0 | |
| 137 | H | n-Pen | 0 | |
| 138 | H | n-Hex | 0 | |

Preparation Examples (Starting Materials)

Example (A)

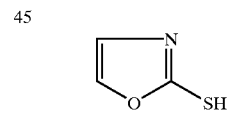

16.5 g of potassium thiocyanate were added to 400 ml of ethanol, to which 15 ml of concentrated hydrochloric acid was added little by little under cooling and stirred for 1 hour. An ethanol solution of thiocyanic acid was obtained by filtration of the reaction mixture. In another flask 300 ml of water and 19.0 g of dihydroxyfumaric acid were stirred at 60° C. for 1 hour to obtain an aqueous solution of glycolaldehyde through decarboxylation. The solutions were mixed and refluxed for 15 hours. After the reaction was finished, the solvent was distilled off under reduced pressure and the residue was purified by column chromatography (eluent: ethyl acetate:dichloromethane=1:9) to obtain 4 g of 2-mercaptooxazole as white crystals (yield 30.8%). m.p. 149–150° C.

Example (B)

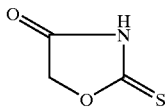

32 ml of 35% formalin, 46 ml of water and 165 ml of concentrated hydrochloric acid were added to a mixture of 65 g of potassium cyanide and 97 g of potassium thiocyanate, and stirred at room temperature for one night. After filtering the deposited crystals, the filtrate was refluxed for 2 hours and alkalized with an aqueous solution of sodium hydroxide. After washing with ether, the solution was acidified with concentrated hydrochloric acid and extracted with ethyl acetate. The ethyl acetate layer was dried with anhydrous sodium sulfate and the solvent was distilled off under reduced pressure to obtain 26.1 g of 4-oxazolidinon-2-thione (yield 18%). {J. Med. Chem. 37(2), 322–8 (1994)}.

Example (C)

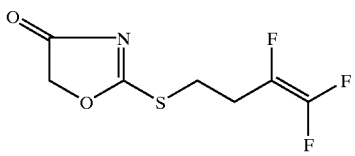

1 g of 4-oxazolidinon-2-thione and 1.8 g of triethylamine were dissolved in 43 ml of tetrahydrofuran, to which 1.9 g of 4-bromo-1,1,2-trifloro-1-butene and 0.2 g of 4-dimethylaminopyridine were added and refluxed for 4 hours. After cooling and distilling off the solvent under reduced pressure, ether and water were added and stirred vigorously. After washing the ether layer with aqueous solution of sodium hydroxide and dried with anhydrous sodium sulfate, the solvent was distilled off under reduced pressure. The residue was treated by column chromatography (eluent: dichloromethane) to obtain 1 g of 2-(3,4,4-trifluoro-3-butenylthio)oxalin-4-one (yield 52%). $n^{20}_D$= 1.4964.

Example (D)

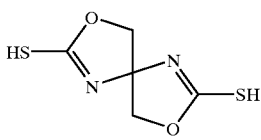

40 ml of concentrated hydrochloric acid was added little by little to a suspension of 35.0 g of potassium thiocyanate in 300 ml of ethanol, under ice cooling and sirred for 1 hour. By filtering the deposited crystals, an ethanol solution of thiocyanic acid was obtained. A solution of 15.0 g of dihydroxyacetone in 100 ml of ethanol was added to the above-mentioned ethanol solution of thiocyanic acid and refluxed for 15 hours. After finishing the reaction, the solvent was distilled off under reduced pressure and the residue was washed with 100 ml of dichloromethane and filtered. The filtered crystals were recrystallized from ethanol to obtain 28.4 g of 3,8-dioxa-1,6-diazaspiro[4,4]nona-1,6-diene-2,7-dithiol (yield 89.6%). mp. 200–202° C.

Example (E)

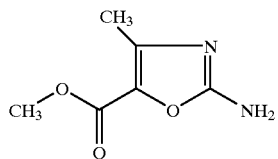

150 g of methyl 2-chloroacetoacetate and 180 g of urea were dissolved in 600 ml of methanol and refluxed for 36 hours. After cooling, the deposited crystals were filtered, suspended in 2N sodium hydroxide solution and extracted with ethyl acetate. After washing with water and drying with anhydrous sodium sulfate, the solvent was distilled off under reduced pressure. The residue was recrystallized from acetonitrile to obtain 10 g of 2-amino-5-methoxycarbonyl-4-methyloxazole. mp. 199–201° C. (point of decomposition).

Example (F)

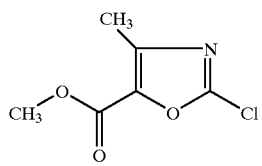

To a suspension of 4.84 g of cupric chloride and 3.4 g of tert-butyl nitrite in 150 ml of acetonitrile, 4.7 g of 2-amino-5-methoxycarbonyl-4-methyloxazole was added at below 10° C. under argon stream and stirred at room temperature for 2 hours. After treatment with 2N hydrochloric acid, the mixture was extracted with ether, washed with water, dried with anhydrous sodium sulfate and the solvent was distilled off under reduced pressure. The residue was treated by silica gel column chromatography to obtain 2.1 g of 2-chloro-5-methoxycarbonyl-4-methyloxazole. mp. 69–71° C.

Use Examples

Example 1

Test Against Meloidogyne spp. (Soil Pot Test)

Preparation of Test Agent:

1 Part of the active compound is impregnated to 99 parts of pumice to make fine granules.

Test Method:

A compound of the formula (I) was added to the soil contaminated by *Meloidogyne incognita* so that the chemical concentration would be 10 ppm and homogeneously mixed by stirring. A pot (1/5000 are) was filled with the soil. About 20 seeds of tomato (variety: Kurihara) were sown per pot. After cultivation in a greenhouse for 4 weeks, they were carefully pulled out not to damage the roots and the root knot index and the controlling effect were determined as follows.

Degree of damage

0: No knot was formed

1: A few knots were formed

2: Knots were formed to a medium extent

3: Knots were formed to an intense extent

4: Knots were formed to the most intense extent (corresponds to non-treatment).

$$\text{Root knot index} = \frac{\sum (\text{degree of damage} \times \text{number of individuals})}{\text{Total number of tested individuals} \times 4} \times 100$$

$$\text{Controlling effect} = \frac{\begin{pmatrix} (\text{Root knot index at non-treated area} - \\ \text{Root knot index at treated area}) \end{pmatrix}}{(\text{Root knot index at non-treated area})} \times 100$$

Evaluation of the ability of the tested compounds to control the nematodes was done according to the values obtained for the controlling effect and with the following standards.

a: Controlling effect 100–71%
b: Controlling effect 70–50%
c: Controlling effect less than 50%
d: Controlling effect 0%

In this test, the compounds of the Preparation Examples 1, 2, 3, 4, 5, 6, 8, 16, 17, 18, 19, 20, 21, 39, 46, 52, 54, 64, 65, 71, 75, 78, 80, 86, 96, 108, 110 and 127 showed controlling effect a.

Formulation Examples

Example a)

(Granule)

To a mixture of 10 parts of a compound of the present invention (e.g. Example. 1), 30 parts of bentonite (montmorillonite), 58 parts of talc and 2 parts of ligninsulfonate salt, 25 parts of water are added, well kneaded, made into granules of 10–40 mesh with the help of an extrusion granulator and dried at 40–50° C. to obtain granules.

Example b)

(Granule)

95 parts of clay mineral particles having particle diameter distribution of 0.2–2 mm are put into a rotary mixer. While rotating it, 5 parts of a compound according to the present invention (e.g Example 2) are sprayed together with a liquid diluent, wetted uniformly and dried at 40–50° C. to obtain granules.

Example c (Emulsifiable Concentrate)

30 parts of a compound according to the present invention (e.g. Example 3), 55 parts of xylene, 8 parts of polyoxyethylene alkyl phenyl ether and 7 parts of calcium alkylbenzenesulfonate are mixed and stirred to obtain an emulsifiable concentrate.

Example d)

(Wettable Powder)

15 parts of a compound according to the present invention (e.g. Example 1), 80 parts of a mixture of white carbon (hydrous amorphous silicon oxide fine powders) and powder clay (1:5), 2 parts of sodium alkylbenzenesulfonate and 3 parts of sodium alkylnaphthalenesulfonate-formalin-condensate are crushed and mixed to obtain a wettable powder.

What is claimed is:
1. A compound of the formula (I)

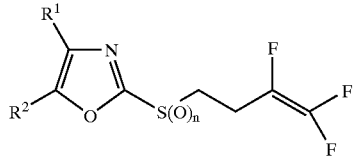

wherein
$R^1$ represents hydrogen; halogen; alkyl that is unsubstituted or substituted with halogen, hydroxy, alkoxy, alkylthio, alkylcarbonyloxy, haloalkylcarbonyloxy, or cyano; or alkylsulfonyloxy;
$R^2$ represents hydrogen; halogen; alkyl that is unsubstituted or substituted with alkoxy or halogen; or alkoxycarbonyl; and
n represents 0, 1, or 2,
with the proviso that if $R^1$ represents alkyl, then $R^2$ does not represent halogen.

2. A compound of the formula (I) according to claim 1 wherein
$R^1$ represents hydrogen; halogen; $C_{1-6}$ alkyl that is unsubstituted or substituted with halogen hydroxy, $C_{1-3}$ alkoxy, $C_{1-3}$ alkylthio, $C_{1-3}$ alkylcarbonyloxy, trifluoromethylcarbonyloxy or cyano; or $C_{1-4}$ alkylsulfonyloxy;
$R^2$ represents hydrogen; halogen; $C_{1-6}$ alkyl that is unsubstituted or substituted with $C_{1-3}$ alkoxy or halogen; or $C_{1-4}$ alkoxycarbonyl; and
n represents 0 or 2.

3. A compound of the formula (I) according to claim 1 wherein
$R^1$ represents hydrogen; fluoro, chloro, or bromo; $C_{1-4}$ alkyl that is unsubstituted or substituted with fluoro, chloro, bromo, hydroxy, $C_{1-3}$ alkoxy, $C_{1-3}$ alkylthio, $C_{1-3}$ alkylcarbonyloxy, trifluoromethylcarbonyloxy or cyano; or methylsulfonyloxy or ethylsulfonyloxy;
$R^2$ represents hydrogen; fluoro, chloro, or bromo; $C_{1-4}$ alkyl that is unsubstituted or substituted with $C_{1-3}$ alkoxy or bromo; or $C_{1-3}$ alkoxycarbonyl; and
n represents 0.

4. A compound of the formula (I) according to claim 1 wherein
$R^1$ represents hydrogen; halogen; methyl, ethyl, n- or i-propyl, n-, i-, s-, or t-butyl, n-pentyl, or n-hexyl, each of which is optionally substituted with halogen, hydroxy, methoxy, ethoxy, n- or i-propoxy, methylthio, ethylthio, n- or i-propylthio, methylcarbonyloxy, ethylcarbonyloxy, n- or i-propylcarbonyloxy, trifluoromethylcarbonyloxy, or cyano; methylsulfonyloxy, ethylsulfonyloxy, n- or i-propylsulfonyloxy, or n-, i-, s-, or t-butylsulfonyloxy;
$R^2$ represents hydrogen; halogen; methyl, ethyl, n-or i-propyl, n-, i-, s-, or t-butyl, n-pentyl, or n-hexyl, each of which is optionally substituted with methoxy, ethoxy, n- or i-propoxy, or halogen; or methoxycarbonyl, ethoxycarbonyl, n- or -propoxycarbonyl or n-, i-, s-, or t-butoxycarbonyl; and
n represents 0, 1 or 2.

5. A compound of the formula (I) according to claim 1 wherein
$R^1$ represents hydrogen; fluoro, chloro, or bromo; methyl, ethyl, n- or i-propyl, or n-, i-, s-, or t-butyl, each of which is optionally substituted with fluoro, chloro, bromo, hydroxy, methoxy, ethoxy, n- or i-propoxy, methylthio, ethylthio, n- or i-propylthio, trifluoromethylcarbonyloxy, or cyano; or methylsulfonyloxy or ethylsulfonyloxy;

$R^2$ represents hydrogen; fluoro, chloro, or bromo; methyl, ethyl, n- or i-propyl, or n-, i-, s-, or t-butyl, each of which is optionally substituted with methoxy, ethoxy, n- or i-propoxy, or bromo; or methoxycarbonyl, ethoxycarbonyl, or n- or i-propoxycarbonyl; and n represents 0, 1 or 2.

6. A process for preparing a compound of formula (I) according to claim 1 comprising (a) for compounds of formula (I) in which
   $R^1$ represents hydrogen; or alkyl that is optionally substituted with halogen, hydroxy, alkoxy, alkylthio, alkylcarbonyloxy, haloalkyl-carbonyloxy, or cyano;
   $R^2$ represents hydrogen or alkyl that is optionally substituted with alkoxy or halogen; and
   n represents 0,
reacting a compound of the formula (II)

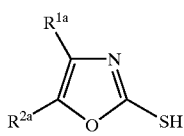

(II)

wherein
   $R^{1a}$ represents hydrogen; or alkyl that is optionally substituted with halogen, hydroxy, alkoxy, alkylthio, alkylcarbonyloxy, haloalkyl-carbonyloxy, or cyano;
   $R^{2a}$ represents hydrogen or alkyl that is optionally substituted with alkoxy or halogen; and
   n represents 0,
with 4-bromo-1,1,2-trifluoro-1-butene in the presence of an inert solvent and optionally in the presence of an acid binder; or (b) for compounds of formula (I) in which
   $R^1$ represents hydrogen; or alkyl that is optionally substituted with halogen, hydroxy, alkoxy, alkylthio, alkylcarbonyloxy, haloalkyl-carbonyloxy, or cyano;
   $R^2$ represents hydrogen or alkyl that is optionally substituted with alkoxy or halogen; and
   n represents 1 or 2,
oxidizing a compound of the formula (Ia)

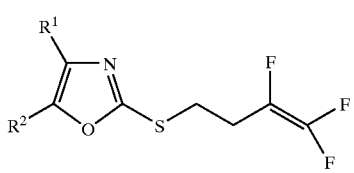

(Ia)

wherein
   $R^1$ represents hydrogen; or alkyl that is optionally substituted with halogen, hydroxy, alkoxy, alkylthio, alkylcarbonyloxy, haloalkylcarbonyloxy, or cyano; and
   $R^2$ represents hydrogen or alkyl that is optionally substituted with alkoxy or halogen, in the presence of an inert solvent; or (c) for compounds of formula (I) in which
   $R^1$ represents hydrogen or haloalkyl;
   $R^2$ represents halogen; and
   n represents 0,
reacting a compound of the formula (Ib)

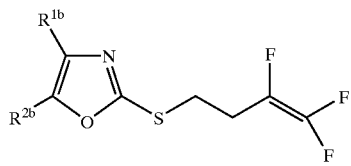

(Ib)

wherein
   $R^{1b}$ represents hydrogen or alkyl; and
   $R^{2b}$ represents hydrogen,
with a halogenating agent in the presence of an inert solvent; or (d) for compounds of formula (I) in which
   $R^1$ represents haloalkyl;
   $R^2$ represents hydrogen or haloalkyl; and
   n represents 0,
reacting a compound of the formula (Ic)

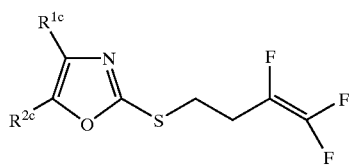

(Ic)

wherein
   $R^{1c}$ represents alkyl; and
   $R^{2c}$ represents hydrogen or alkyl,
with a halogenating agent in the presence of an inert solvent; or (e) for compounds of formula (I) in which
   $R^1$ represents halogen;
   $R^2$ represents hydrogen or alkyl; and
   n represents 0,
reacting a compound of the formula (III)

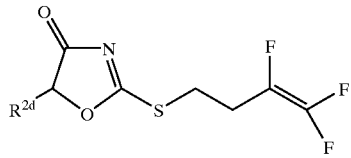

(III)

wherein $R^{2d}$ represents hydrogen or alkyl,
with a halogenating agent in the presence of an inert solvent and optionally in the presence of an organic base; or (f) for compounds of the formula (I) in which
   $R^1$ represents alkylsulfonyloxy;
   $R^2$ represents hydrogen or alkyl; and
   n represents 0, reacting a compound of formula (III)

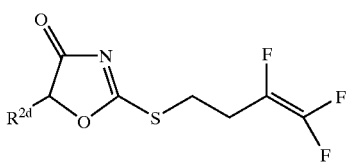
(III)

wherein $R^{2d}$ represents hydrogen or alkyl, with a compound of the formula

 (IV)

wherein $R^{2d}$ represents alkyl,
in the presence of an inert solvent and optionally in the presence of an inorganic or organic base; or (g) for compounds of formula (I) in which
$R^1$ represents alkyl;
$R^2$ represents alkoxycarbonyl; and
n represents 0,
reacting a compound of the formula (IV)

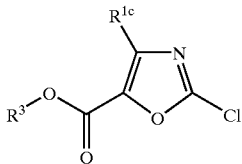
(V)

wherein
$R^{1c}$ represents alkyl; and
$R^3$ represents alkyl, with thiourea to form a product that is then reacted with 4-bromo-1,1,2-trifluoro-1-butene in the presence of an inert solvent; or (h) for compounds of formula (I) in which
$R^1$ represents hydrogen;
$R^2$ represents alkoxyalkyl; and
n represents 0,
reacting a compound of the formula (Id)

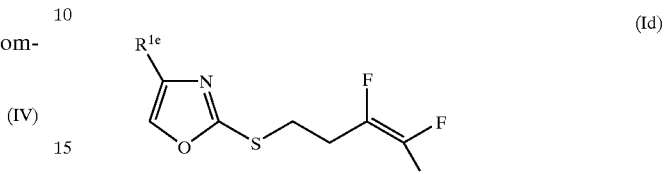
(Id)

wherein $R^{1e}$ represents hydrogen,
with a compound of the formula (VI)

 (VI)

wherein $R^4$ represents alkoxyalkyl, in the presence of an inert solvent.

7. A nematicidal composition comprising at least one trifluorobutene of the formula (I) of claim 1 and one or more extenders.

8. A process for combating nematodes comprising allowing an effective amount of a formulation or application form comprising 0.000001 to 100% by weight of a trifluorobutene of the formula (I) of claim 1 act on nematodes and/or the habitat of nematodes.

* * * * *